United States Patent
Walker

(10) Patent No.: US 11,046,925 B2
(45) Date of Patent: Jun. 29, 2021

(54) SYSTEM AND PROCESS FOR PRODUCING BIOGAS FROM AN ETHANOL SLURRY MIX

(71) Applicant: Dx Resources, LLC, Tampa, FL (US)

(72) Inventor: David R. Walker, Clearwater, FL (US)

(73) Assignee: Dx Resources, LLC, Tampa, FL (US)

( * ) Notice: Subject to any disclaimer, the term of this patent is extended or adjusted under 35 U.S.C. 154(b) by 0 days.

(21) Appl. No.: 16/682,457

(22) Filed: Nov. 13, 2019

(65) Prior Publication Data
US 2020/0148988 A1    May 14, 2020

Related U.S. Application Data

(60) Provisional application No. 62/760,549, filed on Nov. 13, 2018.

(51) Int. Cl.
| | |
|---|---|
| B01D 3/38 | (2006.01) |
| C02F 3/28 | (2006.01) |
| C12P 7/14 | (2006.01) |
| C12M 1/107 | (2006.01) |
| C12M 1/00 | (2006.01) |

(52) U.S. Cl.
CPC .............. C12M 21/04 (2013.01); B01D 3/38 (2013.01); C02F 3/28 (2013.01); C12M 43/08 (2013.01); C12P 7/14 (2013.01)

(58) Field of Classification Search
CPC ...... C12M 21/04; C12M 43/08; C12M 45/00; C12M 43/00; C02F 3/28; B01D 3/38; B01D 3/002; C12P 7/14; C12P 5/023; Y02E 50/30
USPC .................. 210/603; 435/161, 164, 165, 163
See application file for complete search history.

(56) References Cited

U.S. PATENT DOCUMENTS

| | | | | |
|---|---|---|---|---|
| 5,792,355 | A | * | 8/1998 | Desjardins ............ C02F 3/1263 210/605 |
| 6,106,673 | A | | 8/2000 | Walker |
| 8,153,006 | B1 | * | 4/2012 | Fessler .................. C12M 43/02 210/603 |
| 2009/0176289 | A1 | * | 7/2009 | Friedmann ............. C12M 47/18 435/167 |
| 2010/0221804 | A1 | * | 9/2010 | Veit .......................... C12P 7/10 435/165 |
| 2011/0237778 | A1 | * | 9/2011 | Reaney .................... C07K 1/30 530/370 |
| 2014/0065685 | A1 | * | 3/2014 | Rosenberger ............ C12P 7/14 435/162 |
| 2015/0087041 | A1 | * | 3/2015 | Parten .................... B01D 3/002 435/165 |

\* cited by examiner

*Primary Examiner* — Fred Prince
(74) *Attorney, Agent, or Firm* — Boyle Fredrickson S.C.

(57) ABSTRACT

Biogas production from the anaerobic digestion of juice in an ethanol production plant is maximized by mixing a juice containing thin stillage and/or water with a concentrated syrup prior to the anaerobic digestion. The juice then can be mixed with a biomass such as corn meal and enzymes to form a slurry suitable for fermentation. Sufficient syrup is mixed into the juice to provide a BOD concentration in the juice between 100,000 and 150,000 ppm. Enough biogas can be produced to supply enough energy to meet all of the boiler steam production/distillation energy/electrical generation demands for the ethanal production plant with some excess biogas left over for other uses.

18 Claims, 2 Drawing Sheets

SYSTEM AND PROCESS FOR PRODUCING BIOGAS FROM AN ETHANOL SLURRY MIX

CROSS REFERENCE TO A RELATED APPLICATION

This non-provisional application claims benefit under 35 U.S.C. section 119(e) to U.S. Provisional Patent Application Ser. No. 62/760,549; Filed Nov. 13, 2018 and entitled System and Process for Producing Biogas from an Ethanol Slurry Mix, the subject matter of which is hereby incorporated by reference in its entirety.

BACKGROUND OF THE INVENTION

1. Field of the Invention

The invention relates to biogas production and, more particularly, relates to a system and process for producing biogas from a mix or juice used as a liquid source of a slurry used in the production of ethanol from a biomass such as corn.

2. Discussion of the Related Art

Slurries are used in both the dry milling and the wet milling of corn during an ethanol production process. In the dry milling process, corn is ground into meal, which is then slurried by adding water. Enzymes are added to the resultant mash that convert starch to dextrose. Ammonia is added to control the pH and as a nutrient for the yeast, which is added later. The mixture is processed at high-temperatures to reduce the bacteria levels and transferred and cooled in fermenters. Yeast is added to convert sugar to ethanol and carbon dioxide. In wet milling, corn grain is steeped in a dilute combination of sulfuric acid and water for 24 to 48 hours in order to separate the grain into many components. The slurry then is sent through a series of grinders to separate out the corn germ. The remaining slurry or mash then is distilled to produce ethanol.

Whether the slurry is produced by wet milling or dry milling, the slurry ultimately is fermented and distilled in columns to produce ethanol and a mix of water and solids known as "whole stillage." The whole stillage contains solids from the grain and added yeast, as well as liquid from the water added during the process. The whole stillage is decanted to form "thin stillage" (a liquid with 5-10% solids) and wet distiller's grain. The thin stillage can be used as "backset" or a source of liquid for the wet or dry milled slurry.

Thin stillage contains biological components capable of conversion to biogas in an anaerobic digester. However, heretofore, insufficient quantities of biogas could be recovered from thin stillage to justify the cost of incorporating an anerobic digester into an ethanol production plant.

SUMMARY OF THE INVENTION

In accordance with the invention, biogas production from the anaerobic digestion of components of a mix or "juice" serving as a slurry source for the production of ethanol is maximized by mixing thin stillage and/or water with molasses or another syrup prior to the anaerobic digestion process to form a biogas and a liquid stream. The liquid stream is then mixed with a biomass to form a slurry for use in a mash for fermentation. Enough biogas can be produced to supply sufficient energy to meet most or all the boiler fuel demand for steam production/distillation energy/electrical generation for the ethanal production plant and have some excess biogas left over for other uses.

In the most typical case which juice contains thin stillage, i.e., backset, the flow rate of backset to the slurry mix typically varies from 28% to 50% of the total thin stillage production. The remaining thin stillage can be sent to the evaporator of the ethanol production plant to make syrup.

If the ethanol is produced in a dry mill ethanol production process, the juice may additionally contain some or all of the condensate from the evaporator and condensates from the rectifier bottoms from distillation.

The syrup may be a concentrated corn syrup recovered from the evaporator in the ethanol plant or any other syrup, typically containing 15% to 65% solids. It alternatively could be concentrate from other sources such as sugar molasses or blackstrap molasses. The term "syrup" as used herein thus should be understood to mean any liquid that contains sugar. In any event, the syrup has a bio-digestible BOD (biological oxygen demand) load and COD (chemical oxygen demand) load. In the case of concentrated corn molasses, both loads are typically in the neighborhood of 50,000 to 70,000 ppm with the BOD load being a little less than the COD load.

The syrup can be metered into the juice containing the backset and the condensate to increase the levels of BOD needed for cost-effective biogas production. The limitation of the amount of syrup that can be added is the percentage of insoluble solids in each product. In one embodiment, the syrup flow rate into the juice is controlled to achieve a BOD concentration of 100,000 to 150,000 ppm, and most typically of 110,000 ppm.

The discharge liquid stream from the anaerobic digester discharge may screened or otherwise processed to remove insoluble solids, and may be reheated by the incoming juice (all hot in-feeds) in a heat exchanger from 90° F. up to 250° F. This discharge stream is mixed with corn or another biomass to form a slurry.

Corn oil in the backset of a dry-milled corn-based ethanol process may be removed prior to being feed to the anaerobic digester. This removal produces more corn oil, and the quality of all oil production is improved because the oil is not recirculated many times in the plant product. This reduces the formation of free fatty acids in the corn oil.

The use of the juice mix as the feed source of the anerobic digester allows for the anaerobic digester to maximize production of biogas. This has low insoluble solids so as not to drop out solids that could create areas of acidification that can sour in the anaerobic digester pond. The anaerobic digester also may be equipped with multiple recirculation pumps to mix the pond constituents and thus prevent zones of acidification.

The biogas from the digester may be treated by clean up units and/or mixed with natural gas and/or used to fuel boilers and other components of the ethanol plant.

The system and process provide sufficient biogas to supply 80% to 100% of the energy required for the process plant of a dry mill ethanol plant. The use of the biogas permits ethanol production with a "low carbon intensity" industry rating and classification as an "advanced biofuel."

Various other features, embodiments and alternatives of the present invention will be made apparent from the following detailed description taken together with the drawings. It should be understood, however, that the detailed description and specific examples, while indicating preferred embodiments of the invention, are given by way of illustration and not limitation. Many changes and modifications could be made within the scope of the present invention without departing from the spirit thereof, and the invention includes all such modifications.

BRIEF DESCRIPTION OF THE DRAWING

An exemplary embodiment of the invention is illustrated in the accompanying drawings in which like reference numerals represent like parts throughout, and in which.

DETAILED DESCRIPTION

Figure 1A:
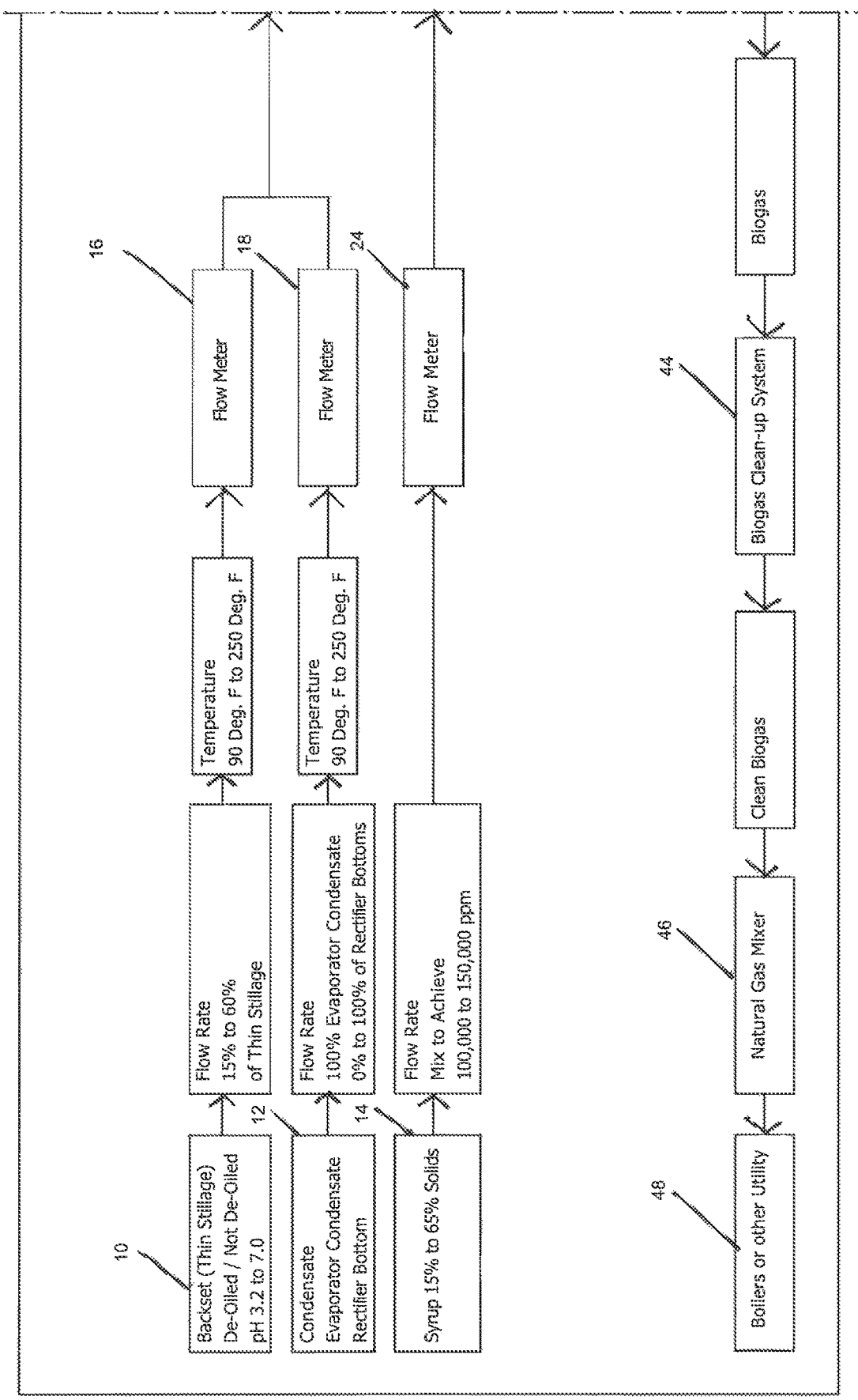
FIGS. 1A and 1B collectively form a block diagram of a slurry mix system and process that maximize the production of biogas.

Referring to the FIGURES, a system and process are schematically illustrated for forming a slurry usable as a distillation source in an ethanol production plant. The slurry includes a biomass capable of fermentation and a liquid mixed with the biomass. In the illustrated embodiment of a dry milled corn ethanol plant, the biomass comprises corn meal, and the liquid comprises a mixed liquid stream or "juice" that is formed from three primary constituent streams 10, 12, and 14. These constituents are thin stillage backset 10, condensate 12 from the ethanol plant, and a concentrated syrup 14, all defined above. In a typical dry-milled corn ethanol plant having a production capacity of 50,000,000 gallons of ethanol per year from corn, the backset and condensate are suppled at a combined rate of about 600-650 gallons/minute including about 400-450 gallons/minute of backset and about 200 gallons/minute of condensate. The backset 10 may contain from 15% to 60%, and more typically about 45%, of the thin stillage produced by the ethanol plant. As discussed above, the remaining thin stillage can be sent to the evaporator of the ethanol production plant to make syrup. The corn oil in the backset 10 may be removed from the backset, possibly upstream from the illustrated components but in any event upstream of the anerobic digester 36, to increase both the volume and the quality of corn oil production by preventing the recirculation of corn oil through the plant and thus reducing the accumulation of free fatty acids in the corn oil. The corn oil can be removed using, for example, the system and process described in U.S. Pat. No. 6,106,673, the subject matter of which is incorporated by reference in its entirety.

The condensate 12 may contain part or all of the evaporator condensate and from none to all of the rectifier bottoms from the ethanol plant. This condensate typically is too acidic for use in a hot water boiler or another application in which the condensate must be reheated, but its acidity renders it well-suited for acidification of the juice during the anerobic digestion process.

It should be noted that other sources of water could be supplied to the juice instead of or in addition to the condensate. It is also possible to use only water and syrup, omitting the backset. However, this process would require high volumes of concentrated syrup.

Typically, both the backset 10 and the condensate 12 streams entering the mix will be at temperatures of 90 to 250° F. Flow rates of the backset 10 and condensate 12 are monitored by respective flow meters 16 and 18 so that the total flow rate of juice formed by the combined stream is known. The two streams may be mixed progressively in a static mixer 20 and a mix tank 22 to form the juice. The static mixer 20 may be an in-line spiral device that disrupts laminar flow through a pipe. The mix tank 22 may be a surge tank with a mixer where other additives such as minerals may be added.

The concentrated syrup 14 is added to the juice either upstream or downstream of the static mixer 20. Its flow rate is controlled by a flow meter 24, using flow rate data obtained from the flow meters 16 and 18 to achieve the desired BOD load in the juice based on known BOD content of the syrup. As mentioned above, the BOD concentration of the thus-formed mix may be on the order of 100,000 to 150,000 ppm, and most typically 110,000 ppm. The required flow rate of syrup for a given flow rate of backset and condensate will, of course, depend on the syrup source and the concentration level of the syrup. In the described case in which the combined flow rate of thin stillage and condensate is 600 to 650 gallons/minute and the syrup is concentrated corn molasses, about 70-75 gallons/minute of concentrated corn molasses syrup are required to provide the desired BOD concentration of 110,000 ppm.

Figure 1B:
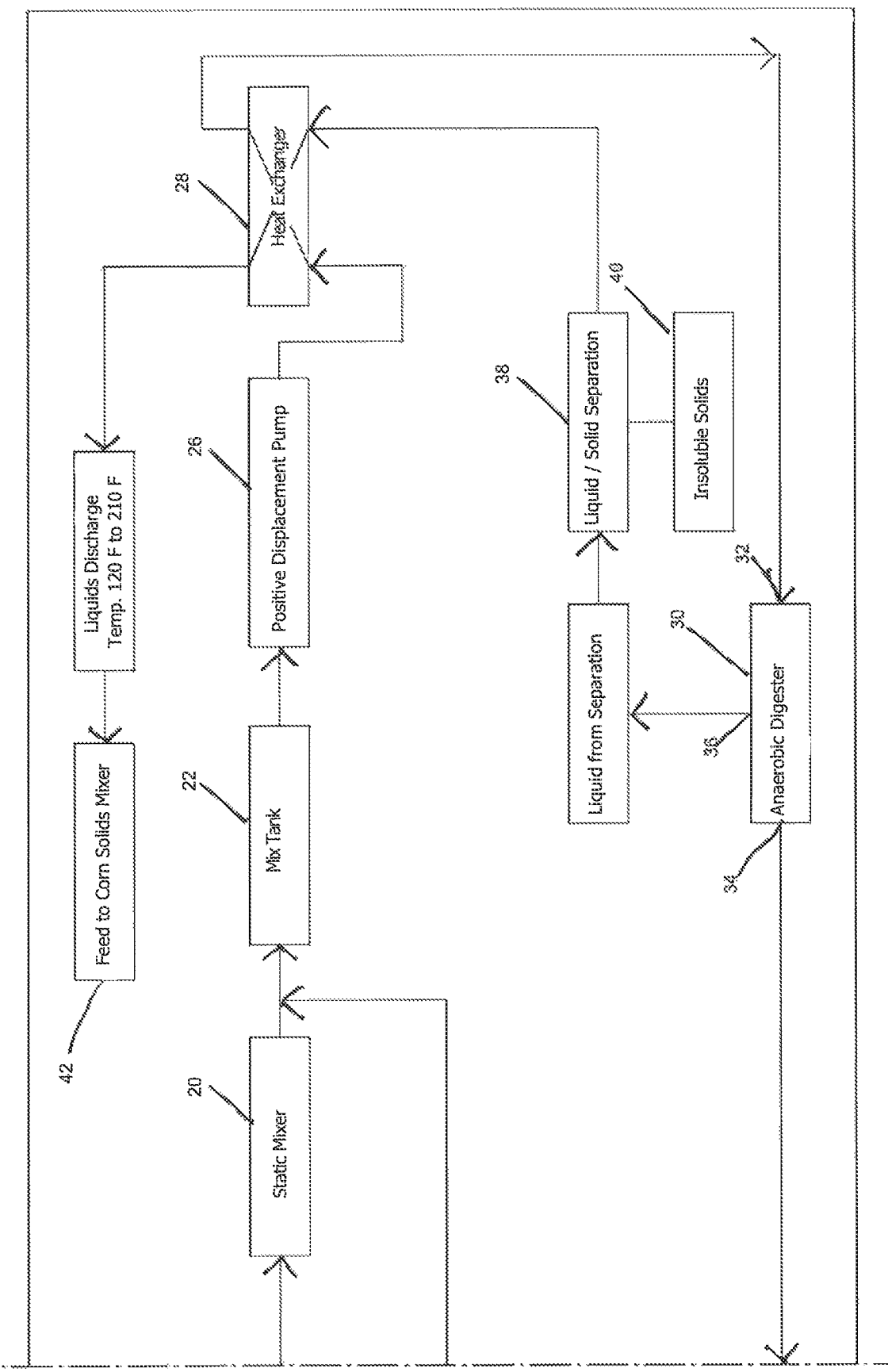

The juice, still at a temperature of about 90 to 250° F., is then pumped by a positive displacement pump 26 through an indirect heat exchanger 28, where it heats the liquid stream being fed to the milled corn from an anerobic digester 30 to 120 to 210° F. The juice has low solids content (on the order of 10-15%) and thus is unlikely to precipitate sufficient solids into the anaerobic digester pond to create areas of acidification that could sour the pond. The juice is then fed to the inlet 32 of the anerobic digester 30 at a temperature of 90-95° F. Biogas is produced in a pond of the digester 30 in a fashion that is, per se, well known, and is drawn off from a biogas outlet 34 of the digester 30. The anaerobic digester 30 may be equipped with multiple recirculation pumps to mix the pond constituents to prevent areas of undesired acidification that could sour the pond. Liquid from the digester 30, typically having a temperature of about 85° F., is pumped off in a stream 36 at the same rate that the juice is suppled (typically at the above-described rate of about 600 to 750 gallons/minute), where a coagulant is added and insoluble solids are removed in device(s) 38 using screens or the like to reduce the solids level in the stream to a level that is on the order of 5-15%. The removed solids then are disposed of or otherwise handled at 40. The liquid exiting the device(s) 38 is then pumped through the heat exchanger 28, where it is heated as described above before being mixed with the corn in a mixer 42 to form a slurry. As can be seen from FIG. 1B and understood from the fact that all thin stillage not fed to the anaerobic digester 30 is fed to the evaporator, liquid from the anerobic digester 30 is the only liquid source for the slurry mixer 42. Because the liquid forming the slurry has no or very few solids, the plant can accommodate more corn solids with a resultant increase in production. The slurry then can be treated with enzymes and otherwise processed to form a mash suitable for fermentation and distillation. The mixer typically will take the form of a mingler in which a dry corn is mixed with liquid to produce a slurry having about 35% solids.

The biogas exiting the outlet 34 of the digester 30 may be used as fuel for other systems of the ethanol plant. In fact, the digester 30 produces enough biogas to supply sufficient energy to satisfy all boiler needs for steam production/distillation energy/electrical generation with enough energy left over for other uses, such as electrical generation. When used as fuel as a boiler or a similar utility 48, the biogas may, depending on the requirements of a particular utility, be supplied in its raw or untreated form or may be cleaned at 44 using a device(s) such as one or more knock out drums for water removal, hydrogen sulfide scrubber(s), etc. The cleaned gas can be pumped up to line pressure and burned in the utility 48 directly and/or first mixed with natural gas in a blender 46. In this case, the biogas typically will form 90-95% of the combined gas stream by volume.

If sufficient syrup is added to bring the BOD concentration in the juice described above to 110,000 ppm, the system can produce over 100,000,000 BTU, over 150,000,000 BTU, and even up to 160,000,000 BTU or more of energy. As mentioned above, this is sufficient energy to operate all boiler fuel usage for steam production/distillation energy/ electrical generation for the ethanal production plant and have some excess biogas for other uses Many changes and modifications could be made to the invention without departing from the spirit thereof. For example, the described process or variations of it could be used in plants that produce ethanol from fermentable biomasses other than corn, such as sugarcane, sorghum, sugar beets, or bagasse.

What is claimed is:

1. A process comprising, in an ethanol production plant:
   (A) mixing a stream of thin stillage produced by the ethanol production plant and a stream of water with a syrup to form a stream of juice;
   (B) feeding the stream of juice to an anaerobic digester and anaerobically digesting components of the juice to form a biogas and a liquid stream; then
   (C) directing the liquid stream from the anaerobic digester to a slurry mixer and mixing the liquid stream from the anaerobic digester with a fermentable biomass to form a slurry for use in a mash for fermentation and distillation.

2. The process of claim 1, wherein the stream of water includes condensate from the ethanol production plant.

3. The process of claim 1, wherein the juice has a BOD of 100,000 to 150,000 ppm.

4. The process of claim 3, wherein the juice has a BOD of about 110,000 ppm.

5. The process of claim 1, further comprising exchanging heat between the stream of juice flowing into the anaerobic digester and the liquid stream from the anaerobic digester.

6. The process of claim 5, wherein the ethanol production plant is a dry milled corn plant having a production capacity of 50,000,000 gallons of ethanol per year, and wherein the biogas provides for over 100,000,000 BTU.

7. The process of claim 1, further comprising fueling components of the ethanol production plant at least in part with the biogas.

8. The process of claim 1, wherein only a portion of thin stillage produced by the ethanol production plant is used to produce the juice, and further comprising sending a remainder of the thin stillage produced by the ethanol production plant to an evaporator of the ethanol production plant.

9. The process of claim 1, wherein the liquid stream from the anaerobic digester is the only liquid mixed with the biomass to form the slurry.

10. The process of claim 1, wherein the juice forming comprises mixing the stream of thin stillage and the stream of water in a first mixer to form a combined stream, then mixing the syrup with the combined stream to form the juice.

11. The process of claim 1, wherein the thin stillage, water, and syrup are mixed in quantities determined to obtain a designated BOD load in the juice.

12. An ethanol production plant, comprising:
   (A) a mixer arrangement that is configured to mix a stream of thin stillage produced by the ethanol production plant and a stream of water with a syrup to form a juice;
   (B) an anaerobic digester that is configured to receive a stream of juice from the mixer arrangement and to anaerobically digest components of the juice to form a biogas and a liquid stream; and
   (C) a slurry mixer that is configured to mix the liquid stream from the anaerobic digester with a fermentable biomass to form a slurry for use in a mash for fermentation and distillation.

13. The ethanol production plant of claim 12, wherein the liquid stream from the anaerobic digester is the only liquid source for the slurry mixer.

14. The ethanol production plant of claim 12, further comprising an evaporator, wherein only a portion of the thin stillage produced by the ethanol production plant is directed to the mixer arrangement, and wherein a remainder of the thin stillage produced by the ethanol production plant is directed to the evaporator.

15. The ethanol production plant as recited in claim 12, wherein the mixer arrangement comprises a first mixer configured to mix the stream of thin stillage and the stream of water to form a combined stream, and a second mixer configured to mix the combined stream with syrup to form the juice.

16. A process comprising, in an ethanol production plant:
   (A) producing thin stillage and condensate;
   (B) mixing a metered quantity of the thin stillage that comprises a first portion of the thin stillage with a metered quantity of condensate and a metered quantity syrup to form a juice having a designated BOD load;
   (C) directing a stream of the juice to an anaerobic digester and anaerobically digesting components of the juice to form a biogas and a liquid stream; then
   (D) mixing the liquid stream from the anaerobic digester with a fermentable biomass, without mixing any of the remainder of the thin stillage with the biomass, to form a slurry for use in a mash for fermentation and distillation.

17. The process of claim 16, further comprising directing the remainder of the thin stillage to an evaporator of the ethanol production plant.

18. The process of claim 16, wherein the juice forming comprises mixing thin stillage and water in a first mixer to form a combined stream, then mixing the combined stream with syrup to form a juice.

* * * * *